United States Patent [19]

Edwards

[11] 4,208,915
[45] Jun. 24, 1980

[54] METHOD OF DETERMINING FOREIGN MATERIAL IN FOOD PRODUCTS USING ULTRASONIC SOUND

[76] Inventor: Bill R. Edwards, 14 Mada Palla Ct., Derby, Kans. 67037

[21] Appl. No.: 7,984

[22] Filed: Jan. 31, 1979

[51] Int. Cl.$^2$ .......................... G01N 29/00; B07C 5/34
[52] U.S. Cl. ........................................ 73/620; 73/639; 209/590
[58] Field of Search ................. 73/620, 624, 625, 627, 73/628, 632, 635, 639, 599, 600; 209/590; 426/238; 99/451, DIG. 12

[56] References Cited

U.S. PATENT DOCUMENTS

| 2,545,101 | 3/1951 | Meunier | 73/639 |
|---|---|---|---|
| 2,836,059 | 5/1958 | Beaujard et al. | 73/620 |
| 3,423,991 | 1/1969 | Collins | 73/639 |
| 3,435,950 | 4/1969 | Suverkrop | 209/590 |
| 3,503,501 | 3/1970 | Seaborn | 209/590 |
| 3,975,261 | 8/1976 | Beck | 209/590 |

FOREIGN PATENT DOCUMENTS

| 1132416 | 6/1962 | Fed. Rep. of Germany | 209/590 |
|---|---|---|---|
| 470239 | 8/1937 | United Kingdom | 209/590 |

*Primary Examiner*—Stephen A. Kreitman
*Attorney, Agent, or Firm*—Edwin H. Crabtree

[57] ABSTRACT

A method of determining foreign material such as metal and bone particles in food products, the method using ultrasonic sound frequencies from a plurality of transducers disposed in a rotatable cylinder having a liquid copulant. The cylinder having a surrounding flexible wall which is compressed on top of the surface of the food products. The sound frequencies are transmitted through the food products and received back by a receiver in the transducers for monitoring any variance in the frequency indicating foreign material in the food products.

6 Claims, 5 Drawing Figures

METHOD OF DETERMINING FOREIGN MATERIAL IN FOOD PRODUCTS USING ULTRASONIC SOUND

BACKGROUND OF THE INVENTION

This invention relates to the use of ultrasonic sound for locating foreign particles in an object and more particularly, but not by way of limitation, to a method of determing foreign materials in food products such as meat, poultry, fish and other products which are susceptible to receiving foreign particles therein before the food products are packed for storage and shipment.

Heretofore, ultrasonic sound frequency using transducers has been greatly used in non-destructive testing and in particular, for determining metallurgical flaws in alloys, weld joints, castings, and other metal materials. Also transducers have been used in rotating tires, balloons, or diaphrams having liquid copulants therein. Specifically, these types of test devices are disclosed in U.S. Pat. No. 2,545,101 to Meunier, U.S. Pat. No. 3,507,308 to White, and U.S. Pat. No. 4,098,132 to Mikesell. Also recent patents have issued using various types of ultrasonic transducers in U.S. Pat. Nos. 4,096,755, 4,096,757, 4,092,868, 4,096,736, 4,098,129 and 4,099,045.

None of the prior art inventions using ultrasonic sound specifically deal with the problem of foreign material in food products and finding the contaminated food product prior to packaging and shipment to the consumer.

The food processing industry has grown rapidly in the recent years due to a growing population and in particular, food products for fast food franchises. Because of the large demand of various types of food products such as meat products, hamburger patties, fish fillets, boneless chicken products, boneless fish products, and the like, a growing concern by the food processing company has been brought about because of potential product liability when foreign material is found by the consumers in their food purchase.

Prior to the subject invention foreign particles were detected in food products on assembly lines and conveyor belts by visual inspection. Visual inspection has been ineffective when foreign particles cannot be seen visually on the surface of the food product or when the inspector is negligent and fails to view the products carefully.

The subject invention provides a method of determining foreign material in food products and automatically rejecting the contaminated food products from the conveyor or processing line.

SUMMARY OF THE INVENTION

The subject method of determining foreign materials in food products substantially reduces the risk of foreign material such as metal, bone particles, hair, cloth, and the like being found in food products by the consumer. The method eliminates the need of having food inspectors for visually checking for contaminated food products.

The invention uses ultrasonic sound frequencies transmitted from a transducer and received by the transducer in a rotatable cylinder having a flexible wall. The wall, when compressed, assumes the shape of the top of the food products so that a proper coupling is made with the food product and sound frequencies can be transmitted through the food products. Any irregular sound frequencies received by the transducer will indicate foreign material in the food product.

The invention can be adapted to various sizes, shapes and lengths of conveyors and food processing lines used in transporting food products prior to packaging and shipping to the consumer.

The invention further provides means for automatically rejecting food products contaminated with foreign materials when unusual sound frequencies are detected in the food product.

The method of determining foreign material in food products using ultrasonic sound frequency detection includes the steps of conveying the food products on a conveyor below a rotatable cylinder which houses a plurality of utlrasonic transducers therein. The cylinder is filled with a liquid sound wave conductor with a surrounding flexible wall which can effectively assume the shape of the top surface of the food products when the flexible wall is compressed thereagainst. When the food products are conveyed under the rotatable cylinder and the flexible wall is compressed against the food products, the transducers transmit ultrasonic frequencies through the liquid conductor, the flexible wall and through the food products. The reflected ultrasonic sound frequencies are received by the receiver in the transducer and any unusual change in sound frequency is monitored. When an unusual sound frequency is received a rejection mechanism is automatically activated for removing the contaminated food product from the conveyor.

The advantages and objects of the invention will become evident from the following detailed description of the drawings when read in connection with the accompanying drawings which illustrate preferred embodiments of the invention.

DETAILED DESCRIPTION OF THE DRAWINGS

Figure 1:
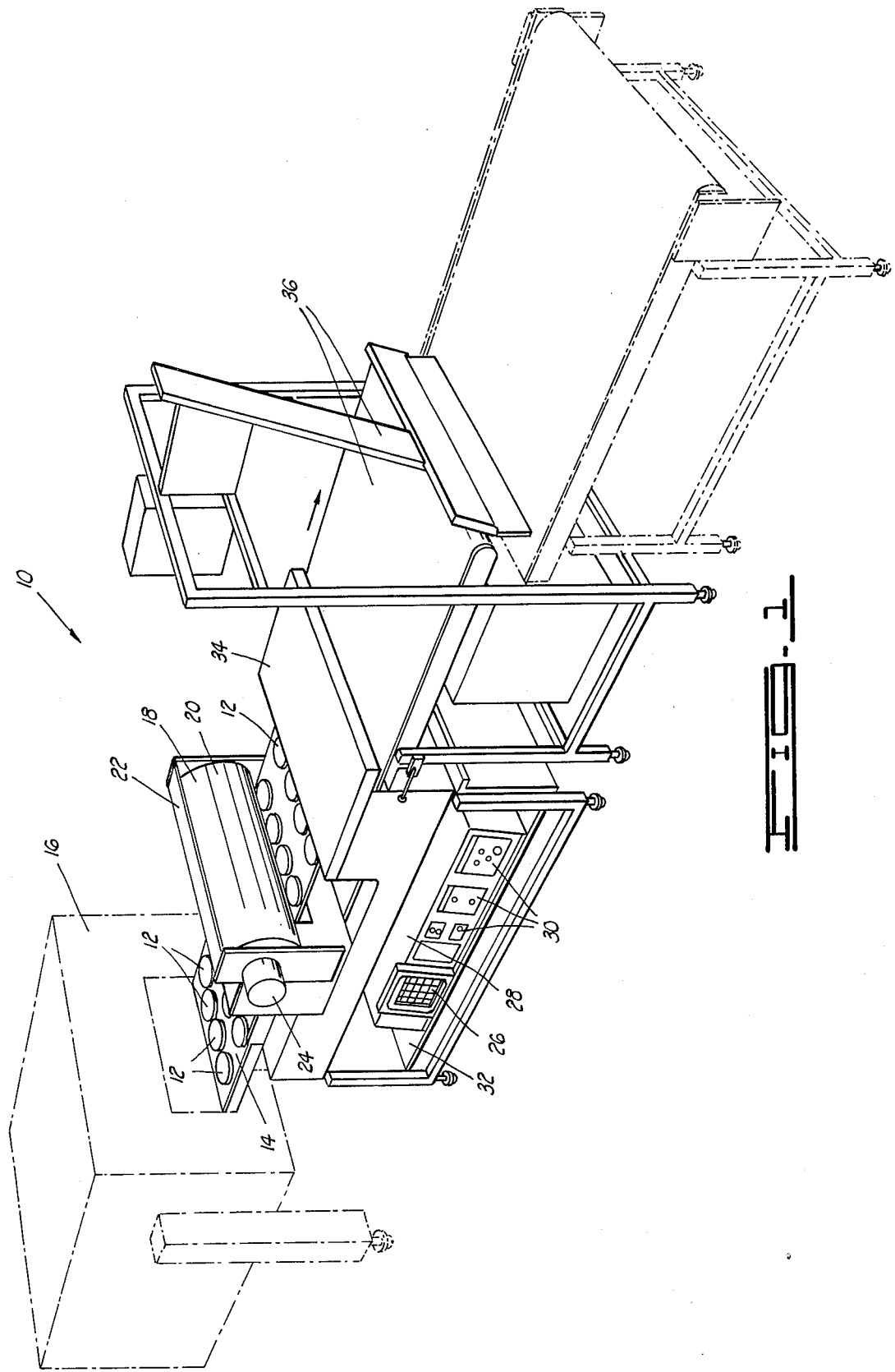
FIG. 1 is a perspective view of a typical hamburger patty conveyor operation receiving frozen hamburger patties from storage and transporting the patties under a rotatable cylinder housing a plurality of ultrasonic transducers.

In FIG. 1 a frozen hamburger patty conveyor system is shown and designated by general reference numeral 10. A plurality of hamburger patties 12 are shown on an endless conveyor 14. The conveyor 14 receives the hamburger patties 12 from a frozen storage area 16. The patties 12 are conveyed under a rotatable hollow cylinder 18 having a flexible wall 20 which can assume the shape of the top surface of the hamburger patties 12 as they are conveyed thereunder. The rotatable cylinder 18 is supported above the conveyor 14 by a U-shaped support 22 having mounted on one side a drive motor 24 for rotating the cylinder 18. The cylinder 18 is electrically wired to a video scanner 26 having a housing 28 with a control panel 30 disposed in front of the housing 28. In this illustration the housing 28 is mounted below the endless conveyor 14 and on a support shelf 32. The scanner 26 is electrically wired to the cylinder 18 and to an automatic hamburger patty rejector 34. The hamburger patty rejector 34, while not shown in detail, may be any standard type of food product rejector having trap doors in the conveyor system or it may have a sweep arm which automatically extends across the conveyor 14 for rejecting the contaminated food product.

From the automatic hamburger patty rejector 34, the patties 12 are conveyed onto a stacker system 36 which provides means for stacking the frozen hamburger patties 12 prior to placing the stacked patties 12 in shipping boses for transporting to the consumer.

As mentioned above, the cylinder 18 is wired to the video scanner 26 and when foreign particles are detected by transducers inside the cylinder 18, the video scanner 26 is electrically alerted for actuating the automatic hamburger patty rejector 34 for removing the contaminated hamburger patty from the conveyor 14.

Figure 2:
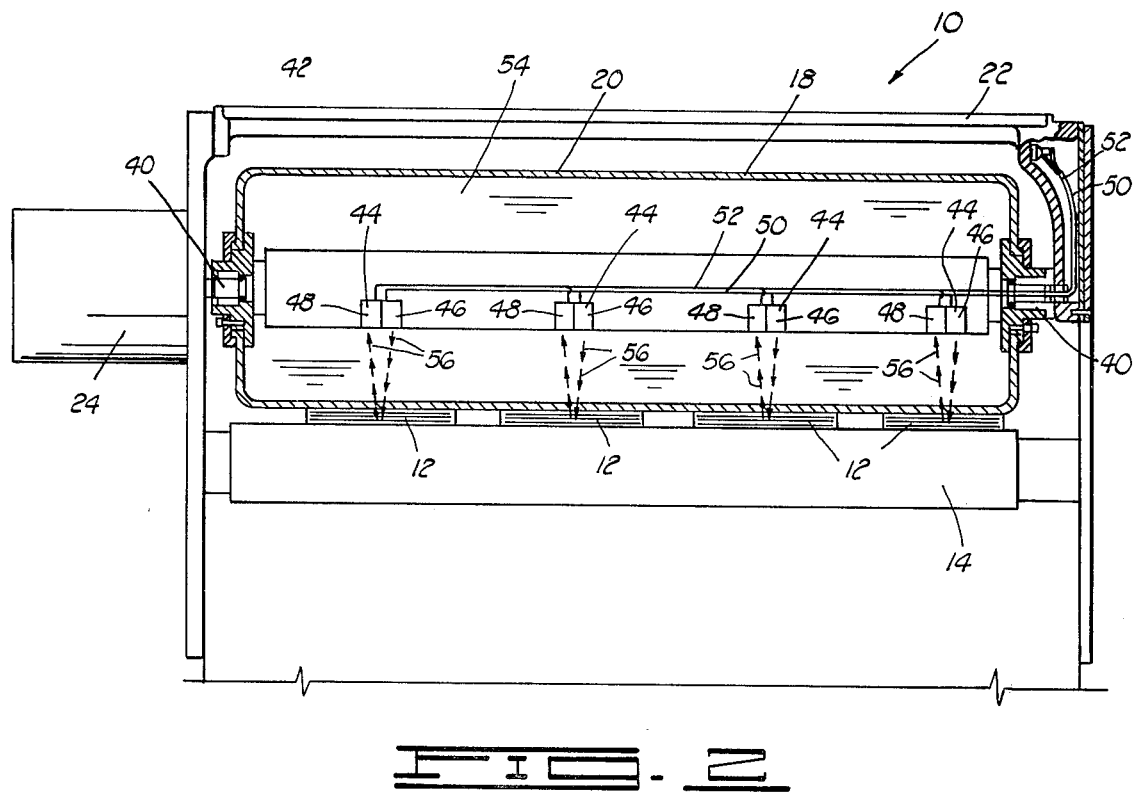
FIG. 2 is a front sectional view of a plurality of transducers mounted in a hollow shaft in a rotatable cylinder mounted above the conveyor belt.

In FIG. 2 a cross section of the cylinder 18 can be seen. The cylinder 20 is rotatably mounted on a drive shaft 40 connected to a drive motor 24. Disposed inside the cylinder 20 is an elongated hollow shaft 42 parallel to and along the rotating axis of the cylinder 20. Mounted inside the hollow shaft 42 are a plurality of transducers 44 having a transmitter 46 and a receiver 48 for transmitting and receiving ultrasonic sound frequencies from the cylinder 18. The transducers 44 are attached to electric leads 50 and 52 which are wired to the video scanner 26 shown in FIG. 1.

Surrounding the hollow shaft 42 and filling the hollow cylinder 20 is a liquid copulant 54 which acts as a conductor for transmitting the ultrasonic sound frequencies shown as arrows 56.

As seen in this view are four hamburger patties 12 riding on top of the endless conveyor 14 with the top surface of the hamburger patties 12 compressed against the sides of the flexbile wall 20 of the cylinder 18.

In operation food products such as the frozen hamburger patties 12 are conveyed below the rotatable cylinder 18 and compressed against the flexible wall 20. The transducers 44 are energized for transmitting ultrasonic sound frequencies downwardly through the liquid copulant 54 through the flexible wall 18, and through the hamburger patties 12 where it is reflected backward toward the receivers 48 which are part of the transducer 44. When the signal of the ultrasonic sound frequencies is received by the transducers 44 it is relayed to the video scanner 26 for detecting any unusual change in the sound frequency in the hamburger patties 12 which would indicate if any foreign material is in the patties 12.

Figure 3:
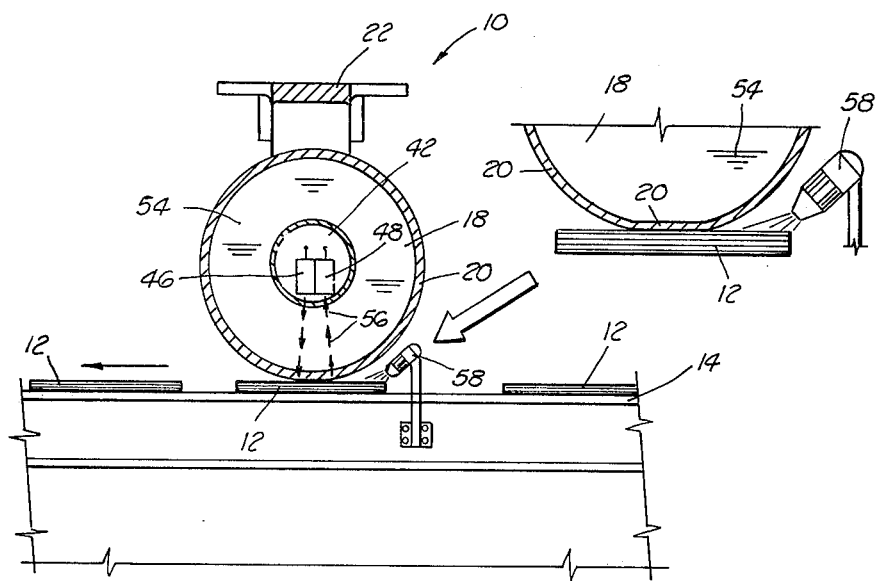
FIG. 3 is a side view of the rotatable cylinder disposed above the hamburger patties on the conveyor belt.

In FIG. 3 a side sectional view of the cylinder 18 is shown. In this view an enlarged portion of the bottom of the cylinder 18 and flexible wall 20 is shown wherein the flexible wall 20 assumes the shape of the top of the hamburger patty 12 so that an effective coupling is made against the food product and the ultrasonic sound frequencies can be conducted therethrough.

To improve the conductance of the ultrasonic sound frequencies a liquid spray may be introduced by a sprayer 58 upstream from the cylinder 18 and attached to the side of the endless conveyor 14. The liquid is sprayed both on top of the frozen hamburger patty 12 and the surface of the flexible wall 18 prior to the wall 18 being rotated on top of the patty 12. The introduction of the liquid on both the surface of the wall 18 and to the top of the patty 12 as mentioned above, improves the conductance of the ultrasonic sound frequencies through the hamburger patties 12.

Figure 4:
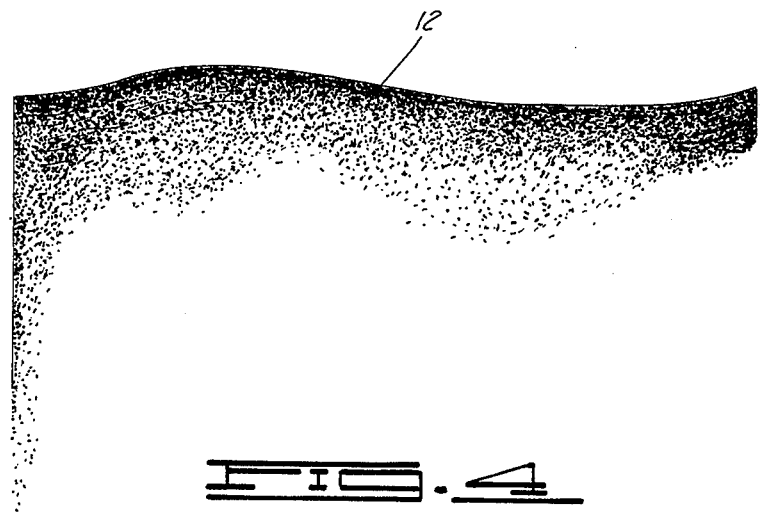
FIG. 4 illustrates a photograph of a typical cross-section of a hamburger patty viewed on a video scanner monitoring the hamburger patties shown in FIG. 1.

In FIG. 4 a photograph is depicted of a typical cross section of a hamburger patty 12 made up by a recording of the ultrasonic sound frequencies illustrating the cross section of the patty 12 indicating that there are no foreign particles detected therein.

Figure 5:
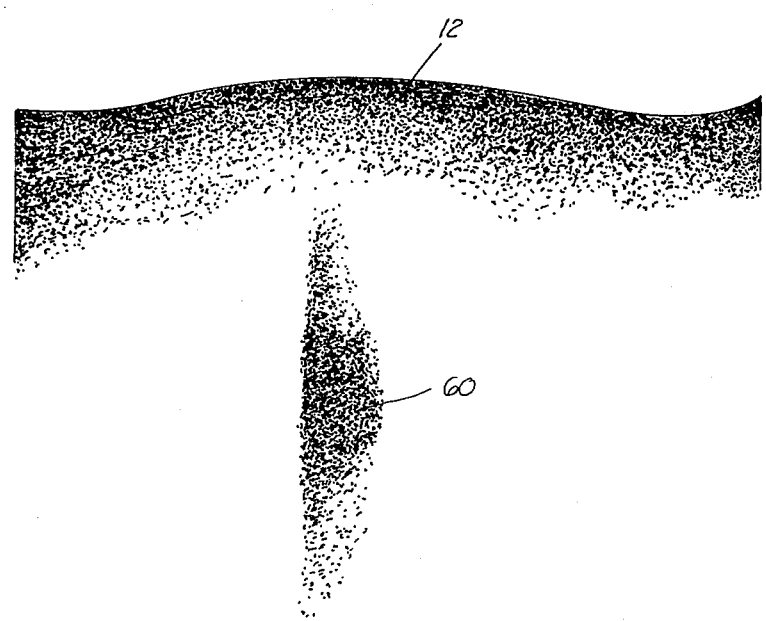
FIG. 5 illustrates a photograph of an example of a foreign particle found in a hamburger patty by the ultrasonic sound frequencies from the transducers.

In FIG. 5 a similar cross section of a depiction of the hamburger patty 12 made up of sound frequencies is shown but having an irregular distortion below the cross section. This distortion is indicated by reference numeral 60 and to a trained observer indicates a foreign material such as metal buckshot, bone particles, or any other foreign matter has been detected and the hamburger patty rejector 34 should be activated so that this foreign matter may be removed from the hamburger patty 12.

While the apparatus shown in FIGS. 1, 2 and 3 illustrate a typical frozen hamburger patty assembly line, it should be appreciated that the method of the invention may work equally well in various types of food product conveyor systems having food products such as frozen meat, fresh meat products, fish, fowl, and other types of food products which are subject to foreign material contamination prior to packaging and shipment of the food products.

It should be noted in FIGS. 2 and 3 the transmission and receiving of the ultrasonic sound frequencies represented by arrows 56 in practice, represent ultrasonic wave lengths in a range of 1.0 to 10.0 megahertz. This range has found to be acceptable for accurately detecting foreign material such as the foreign material 60 shown in FIG. 5.

Changes may be made in the construction and arrangement of the parts or elements of the embodiments as described herein without departing from the spirit or scope of the invention defined in the following claims.

What is claimed is:

1. A method of determining foreign material in food products using ultrasonic sound frequency detection, the steps comprising:
   conveying food products on a conveyor below a rotatable cylinder which houses a plurality of ultrasonic transducers therein, the cylinder filled with a liquid sound frequency copulant, the cylinder having a surrounding flexible wall which can effectively assume the shape of the surface of the food products;
   compressing the flexible wall of the cylinder against the top surface of the food products as the food products are conveyed thereby;
   transmitting ultrasonic sound frequencies from the transducers through the liquid copulant and flexible wall and through the food products; and
   receiving the reflected ultrasonic sound frequencies from the food products by the transducers for determining any unusual change in the sound frequency should there be foreign material in the food product.

2. The method as described in claim 1 wherein the step of transmitting ultrasonic sound frequencies from the transducers includes transmitting the sound frequency in a range of 1.0 to 10.0 megahertz.

3. The method as described in claim 1 further including liquid misting of the cylinder wall and food products prior to compressing the flexible wall of the cylinder against the top of the surface of the food products to aid in providing an adequate copulant between the wall and the top surface of the food products.

4. The method as described in claim 1 further including the step of monitoring the received ultrasonic sound frequency and viewing the sound frequency on a video scanner after the step of receiving the reflected ultrasonic sound frequencies transmitted through the food products.

5. The method as described in claim 4 further including the step of actuating a rejection mechanism for removing the food product contaminated with foreign material, the rejection mechanism disposed adjacent the conveyor and downstream from the rotatable cylinder, the rejection mechanism activated when signaled by the video scanner when the scanner detects a change in sound frequency indicating foreign material in the food product.

6. A method of determining foreign material in food products using ultrasonic sound frequency detection, the steps comprising:

conveying food products on a conveyor below a rotatable cylinder which houses a plurality of ultrasonic transducers therein, the cylinder filled with a liquid sound wave copulant, the cylinder having a surrounding flexible wall which can effectively assume the shape of the surface of the food product;

compressing the flexible wall of the cylinder against the top surface of the food products as the food products are conveyed thereby;

transmitting ultrasonic sound frequencies in a range of 1.0 to 10.0 megahertz from the transducers through the liquid copulant and flexible wall and through the food products;

receiving the reflected ultrasonic sound frequencies from the food products by the transducers for determining any unusual change in the sound frequencies should there be foreign material in the food products; and monitoring the received ultrasonic sound frequencies for unusual change in sound frequencies and actuating a rejection mechanism for removing the contaminated food product, the rejection mechanism disposed adjacent the conveyor and downstream from the rotatable cylinder.

* * * * *